United States Patent [19]
Kobayashi et al.

[11] 4,149,787
[45] Apr. 17, 1979

[54] EYE FUNDUS CAMERA

[75] Inventors: Kazunobu Kobayashi, Yokohama; Shinichi Ohta, Tokyo; Haruhisa Madate, Yokohama, all of Japan

[73] Assignee: Canon Kabushiki Kaisha, Tokyo, Japan

[21] Appl. No.: 747,297

[22] Filed: Dec. 3, 1976

[30] Foreign Application Priority Data

Dec. 8, 1975 [JP] Japan .................. 50-146158

[51] Int. Cl.² .......................................... G03B 29/00
[52] U.S. Cl. ................................. 354/62; 351/7; 354/48
[58] Field of Search ............... 354/23, 48, 62; 351/7, 351/6

[56] References Cited

U.S. PATENT DOCUMENTS

| | | | |
|---|---|---|---|
| 2,947,216 | 8/1960 | Drews | 354/62 X |
| 3,280,714 | 10/1966 | Gunther et al. | 354/55 |
| 3,614,214 | 10/1971 | Cornsweet et al. | 351/7 |
| 3,715,166 | 2/1973 | Leighty et al. | 351/6 X |
| 3,818,494 | 6/1974 | Tanikoshi et al. | 354/43 |
| 3,888,569 | 6/1975 | Munnerly et al. | 351/6 |
| 3,915,564 | 10/1975 | Urban | 354/62 X |
| 3,944,342 | 3/1976 | Martinez | 351/7 X |

*Primary Examiner*—John Gonzales
*Attorney, Agent, or Firm*—Toren, McGeady and Stanger

[57] ABSTRACT

In an eye fundus camera an optical system illuminates the eye fundus and a sensor detects the intensity of reflection from the eye. When the intensity of reflection is sufficient to indicate that the person being examined has blinked his eye, the photographic system is disabled.

17 Claims, 6 Drawing Figures

EYE FUNDUS CAMERA

BACKGROUND OF THE INVENTION

The present invention relates to an eye fundus camera and particularly to a camera which can detect whether an eyelid of a person being examined is open or closed.

Eye fundus cameras have been widely used for examinations in the prevention of adult diseases. However, where the number of photographic frames per person is limited as in a group examination, it is quite important to avoid situations in which a person being examined blinks and his eye fundus is not photographed.

SUMMARY OF THE INVENTION

The present invention achieves an appropriate display or control of the photographic operation by utilizing the fact that the amount of illuminating light reflected from an eye fundus of an eye is less than the amount of light reflected from the eyelid when the eye blinks.

In the present invention, a light receiving means is provided in an eye fundus camera having a photographing light souce and an illuminating system to guide illuminating light from said photographing light source, for receiving a portion of light reflected from an eye to be examined which is illuminated by the illuminating system and for conducting photo-electric conversion, and a display means to display the state of opening or closing of an eyelid of an eye to be examined is actuated by the amount of light detected by said light receiving means.

In the present invention a state in which an eyelid is closed is detected by detecting the difference in the amount of light reflected between a time when an eyelid of an eye to be examined is opened and a time when the same eyelid is closed, and the photographic function is disabled when said eyelid is closed.

The present invention also informs an examiner that an image of an eye fundus is not photographed as an examinee closed his eyelid at a time when photographing mechanism started action.

Further, an eye-bottom camera of the present invention has a light receiving means to receive luminuous flux reflected at a surface of an eye to be examined, a first detection means to process the signal from said light receiving means at a time of ordinary observation of an eye to be examined for detecting the opening or closing of an eyelid of a person being examined, a second detection means to process the signal from said light receiving means at a time of photographing for detecting whether or not an image of the eye fundus of a person to be examined is photographed, a photographing control means to restrict photographing mechanism by the signal from said first detection means, and a display means to display, by the signal from said second detection means, whether or not an image of the eye fundus of a person being examined is photographed.

Also it is desirable to provide a light chopper to make the illuminating light an intermittent light beam with appropriate frequency or a power source having a function to make the illuminating light into a form of pulse for preventing external light other than the illuminating light from forming noise at a time of observation, and to provide within a circuit of said first detection means a band-pass filter for passing electric pulses having same frequency.

Also it is possible in an eye fundus camera of the present invention to use a detection circuit to detect the state of an eyelid of an eye to be examined commonly for detection at a time of observation and for that at a time of photographing.

DETAILED DESCRIPTION OF PREFERRED EMBODIMENT

Figure 1:
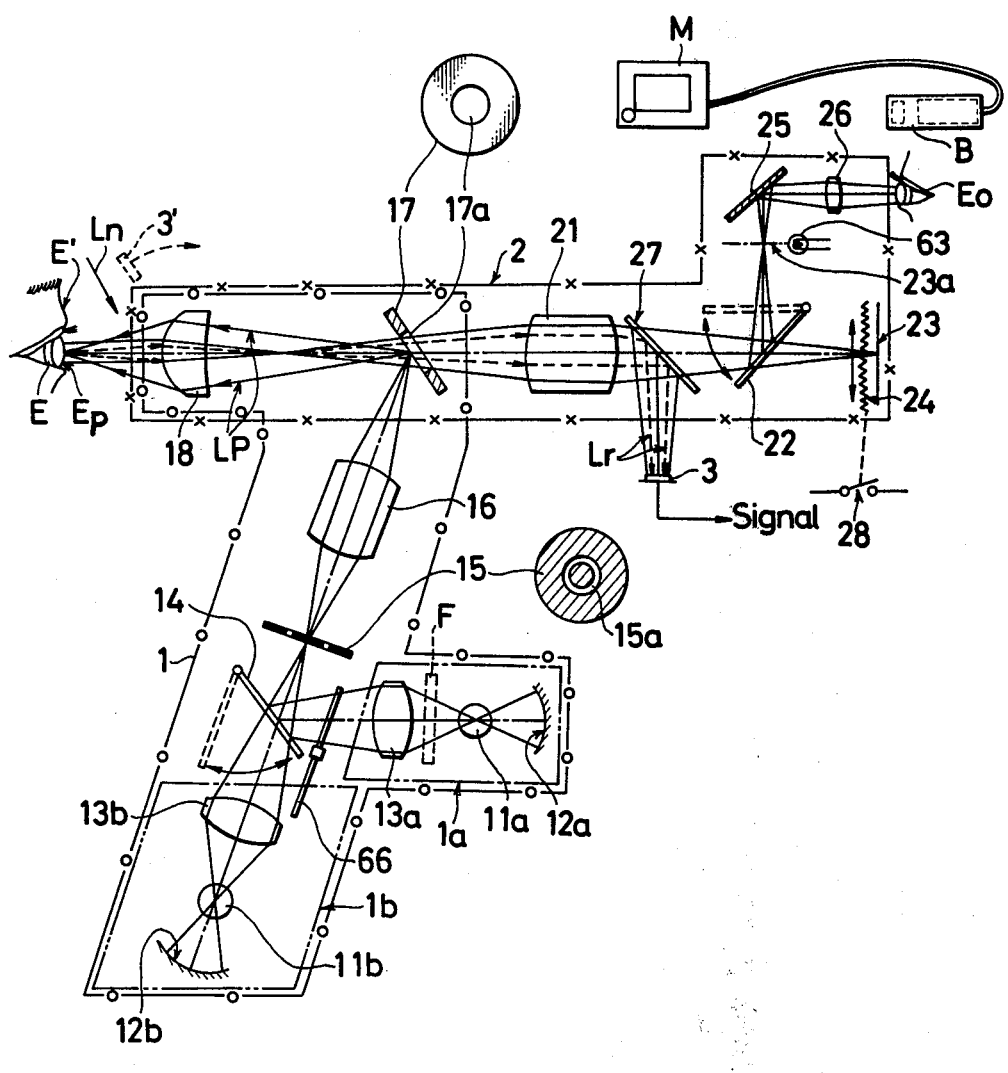
FIG. 1 is a drawing to show an outline of an optical system of an eye fundus camera according to the present invention.
Figure 2:
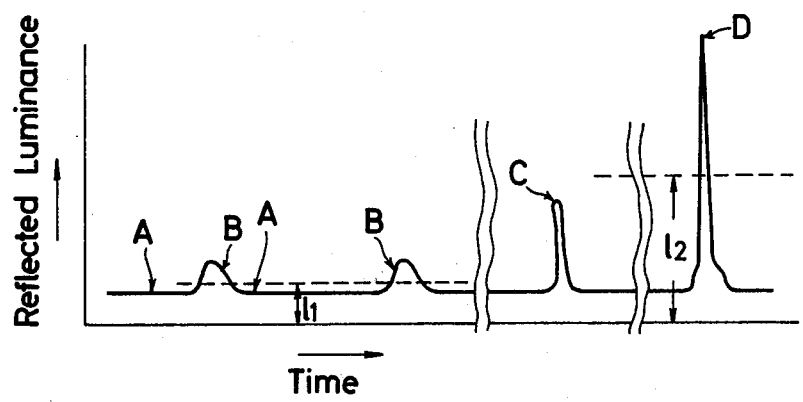
FIG. 2 is a diagram to show variation in the amount of light reflected at a time as an eyelid of a person being examined is opened and at a time as it is closed.
Figure 3:
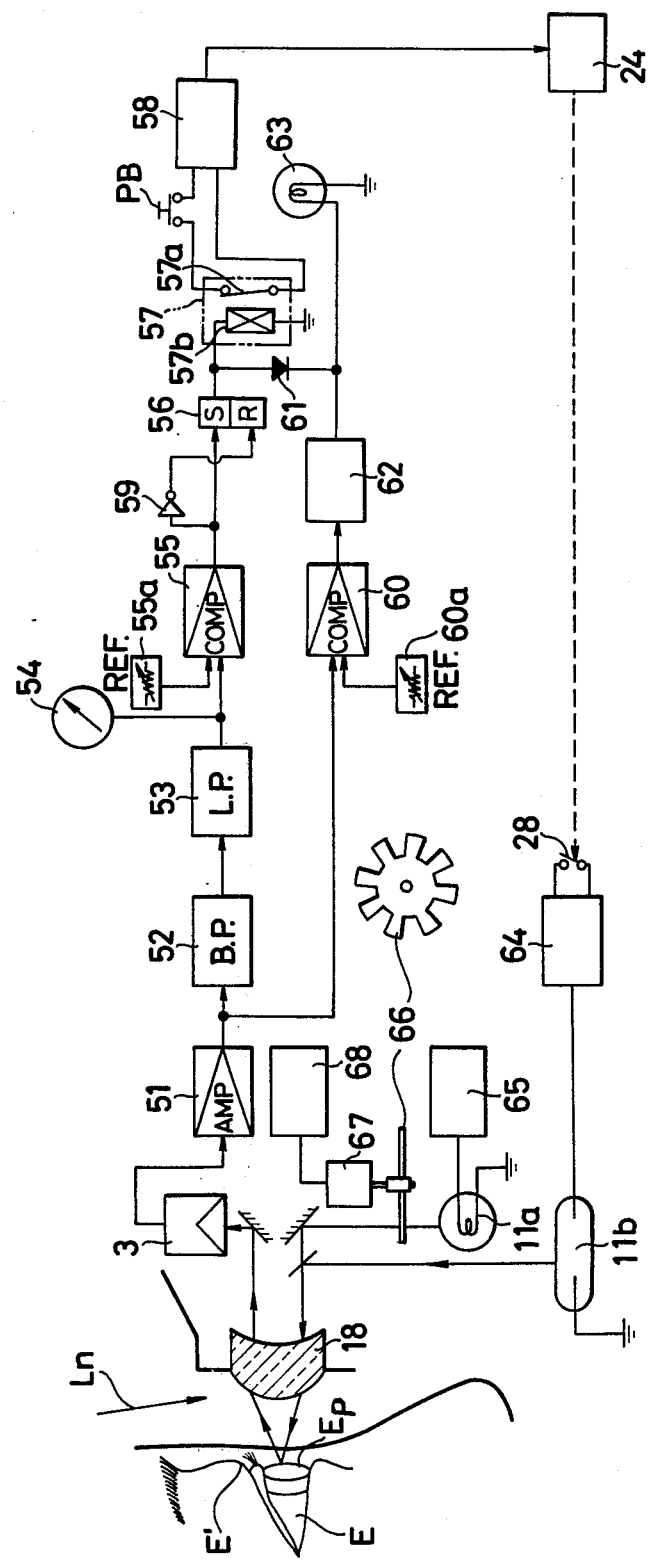
FIG. 3 is a block circuit diagram to show an example of an electric circuit to process the signal from a light receiving element in an eye fundus camera according to the present invention.

FIG. 1 shows vital features of an optical system of an eye fundus camera of the prsent invention. FIG. 2 is a drawing to show how the reflective light detected by the method of FIG. 1 increases by blinking at a time of observation and photographing. FIG. 3 is a block diagram of an electric system to display and indicate the opening or closing of eyelid of a person being examined to an examiner or to control the photographic operation.

In FIG. 1, what is shown as $E_0$ is an eye of an examiner, and what is shown as E is an eye being examined of a person being examined, while E' shows an eyelid of a person being examined and $E_p$ shows a surface of his eyeball. What is shown as 1 is an illumination system unit, and what is shown as 2 is an observation. Forming a part of both an observation system and a photographic system are an objective lens 18 and a mirror 17 with an opening 17a. What is shown as 1a is a light source for observation of the eye fundus, and what is shown as 1b is a light source for photographing the eye fundus, while 11a shows a tungsten bulb for observation, and 11b is a stroboscopic tube. What are shown as 12a and 12b are reflectors, and 13a and 13b are condensor lenses. The light beam from the light sources 1a and 1b consisting of the component elements just mentioned is condensed into a slit light shielding plate 15. A movable mirror 14 guides observation light beam when pivoted to the position shown and guides photographic light beam when moved from the optical path. What is shown as 16 is a relay lens and forms an image of a ring shaped opening 15a of the slit light shielding plate 15 near an opening 17a of the mirror 17 with hole. Said opening 17a is to pass the light reflected from the eye fundus. And the mirror 17 with the opening, said relay lens 16 and said slit light shielding plate 15 are set up for eliminating commonly known light reflected from the surface of the eye fundus.

What is shown as 18 is an objective lens, and the holed mirror 17 and the eyeball surface $E_p$ are in an about conjugate relationship with respect to said objective lens 18. What is shown as 21 is a photo-taking lens, and what is shown as 22 is a movable mirror which sends light beam to a film 23 or an ocular lens 26. Here, the eye fundus of the eye E being examined and the film surface are in conjugate relationship with respect to the objective lens 18 and the photo-taking lens 21. Also what is shown as 23a is a position equivalent to film 23 and is an imaging plane in the air. What is shown as 25 is a mirror which 26 is an ocular lens to see an image in the air.

Further what is shown as 27 is a beam splitter, employing as an example a thin film mirror. What is shown as 3 is a light receiving element provided to detect the variation in the amount of reflected light by blinking, and it is preferably positioned to be conjugate with the eyelid or the eyeball surface $E_p$ with respect to the objective lens 18 and the phototaking lens 21.

On the other hand, what is shown as 24 is a shutter plane, and what is shown as 28 is a synchronizing switch of a stroboscope control circuit what is to be explained below and is to be closed in an association with opening of the shutter plane. The set up of these parts mentioned above is same as in a shutter of an ordinary photographic camera, and as an example an electric shutter in which a lever holding a shutter plane is displaced by magnetizing a magnet and a follower screen closes aperture after an elapse of prescribed period of time, is widely known, thus detailed explanation of said set up is omitted.

What is shown as 63 is a lamp to display an improper state by which blinking of a person being examined can be recognized while observing the eye fundus if said lamp is provided at the position of the imaging plane 23a in the air, while the same can be recognized even after the movablle mirror 22 is retreated to outside of optical path.

In the set up mentioned, the movable mirrors 14 and 22 are at the positions shown by solid lines, and when the observation light source 11a is lighted the eye fundus of the eye E being examined is observed by the examiner $E_o$ by the illuminating light beam $L_p$, and at a same time a portion of light reflected from the eye fundus reaches the light receiving element 3 by the beam splitter 27.

When the person being examined blinks and the eyelid E' covers the eye-ball surface $E_p$, the amount of reflected light received by the light receiving element 3 noticeably increases. Also even after the movable mirrors 14 and 22 are shifted to the positions shown by dotted lines in an association with the release of the photographing switch and the shutter 24 is opened lighting the photographing light souce (stroboscope) 11b, there will exist a definite difference in the amount of reflected light when an eyelid is opened and when said eyelid is closed during blinking.

FIG. 2 shows a manner in which the amount of reflected light varies as time passes by. In this drawing, what is shown as A shows the amount of reflected observation light at a time an eyelid is opened, while B shows the amount of reflected observation light at a time the eyelid is closed. Also C shows the amount of reflected photographing light at a time an eyelid is opened, while D shows the amount of reflected photographing light at a time the eyelid is closed. Therefore blinking can be detected if a light amount level is set at $l_1$ at a time an eye fundus is illuminated by observation light, detecting such amount of light as exceeding said $l_1$, while said light amount level can be set at $L_2$ at a time the eye fundus is illuminated by photographing light. While the level $l_1$ or $l_2$ may be set at same level at that of A or C, the same should better be set at a little higher level since the A itself or C itself varies somewhat.

Next, explanations will be made on the process beyond the light receiving element following FIG. 3. In the drawing, the eye E being examined, the eyelid E', the light receiving element 3 and the objective lens 18 are same as in FIG. 1. And the optical system shown in FIG. 3 is a simplified one showing schematically what is shown in FIG. 1, thus it does not necessarily matches precisely with the optical system shown in FIG. 1. What is shown as 51 is an amplification circuit, and 52 is a band-pass filter, while 53 is a smoothing circuit, and 54 is a meter to inform an improper state. A first comparison and discrimination circuit receives a comparison signal corresponding to the level $l_1$ from a comparison signal generation circuit 55a. The signal is used as a comparison reference signal relative to the input from the smoothing circit 53. Also the meter 54 serves not only to display the state of an eyelid of an eye being examined as being opened or closed, but serves to adjust the size of the signal $l_1$ from said comparison signal generation circuit 55a based on the way the meter 54 swings.

What is shown as 56 is a set-reset-flip-flop circuit and 59 is an inverter circuit. What is shown as 57 is a relay switch and 57a is a normally closed contact always having a load in one direction by a spring not being shown in the drawing, and said normally closed contact 57a is connected to a part of an electric shutter control circuit 58. What is shown as PB is a release button. A second comparison and discrimination circuit 60 receives a comparison signal as corresponding to the above mentioned level $l_2$ from the circuit 60a. The latter signal is used as the comparison reference signal for the input from the amplification circuit 51. A circuit 62 serves to retain its input signal for a prescribed period of time. For example it may be a one shot multivibrator a warning display lamp 63 serves to display that the eye fundus picture of an eye being examined was not taken. What is shown as 64 is a well known type of stroboscope control circuit. A rectifier 61 serves to prevent the current from the circuit 62 from flowing to the relay switch 57. Since the current from the flip-flop circuit 56 flows to the lamp 63 through the rectifier 61, the lamp 63 is lighted when the person being examined closes his eye during observation. If the lamp 63 does not need to be lighted at a time of observation, it is not necessary to connect the first detection circuit to detect the state of eyelid at a time of observation with the second detection circuit to detect the state of eyelid at a time of photographing the eye.

A power source 65 serves for lighting and flickering the lamp 11a, and the illuminating light generated from the lamp 11a is changed into intermittent light of frequency $f_o$ by a sector chopper 66 installed to a synchronizing motor 67 rotated by a motor power source 68. The frequency $f_o$ is same as the frequency passed by the band pass filter 52.

In operation the electric signal corresponding to the amount of reflected light detected by the light receiving element 3 is applied to the meter 54 after going through the amplification circuit 51, the band-pass-filter 52, the smoothing circuit 53, so that the change in the amount of reflected light by blinking can be displayed as the change in the swing of meter pointer.

During this time the effect of any external disturbance is eliminated by flickering the observation light source 11a with the power source 65 for distinguishing the illminating light from said light source from external light Ln.

The smoothing circuit 53 cuts off the high zone of the pulses passing through the band pass filter 52 to smooth the same for stabilizing the means succeeding the same, for example for stabilizing the swing of the pointer of said meter 54.

On the other hand, when the signal from the smoothing circuit 53 is applied to the first comparison and discrimination circuit 55 and the signal exceeding the signal corresponding to the level $l_1$ is inputted, a signal is generated from the first comparison and discrimination circuit 55 to place the flip-flop circuit 56 in set state. A solenoid 57b of the relay switch 57 is magnitized by the signal from the flip-flop circuit 55 and the normally closed contact 57 is opened, thus the circuit is broken.

Therefore even if a release button is pressed when an eyelid is closed, the shutter control circuit 58 will not function, thus the shutter will not function nor the stroboscope emit light.

Figure 4:
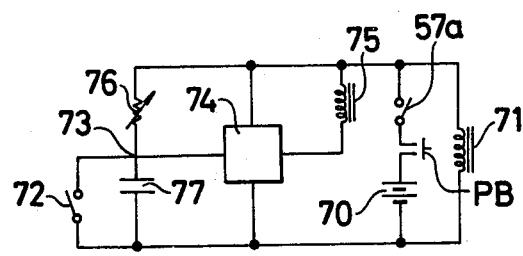
FIG. 4 is a drawing to show an example of a shutter control circuit shown in FIG. 3.

Also when eyelid of an eye being examined is opened, the signal from the first comparison circuit will disappear, therefore the inverter circuit 59 functions to place the flip-flop circuit 56 in a reset state. Therefore the signal from the flip-flop circuit 56 is shielded and the solenoid 57b is demagnetized. Thus the contact 57a is closed by a spring not being shown in the drawing. Therefore as the release button PB is pressed the movable mirrors (14, 22) retreats from an optical path and the shutter control circuit 58 functions. FIG. 4 illustrates an example of the shutter control circuit 58. In FIG. 4, as the shutter button PB is pressed with the contact 57a closed, the current from the power source 70 actuates the magnet 71, thereby unlocking a locking member which normally locks a leader screen of shutter, and causing said leader screen to run. On the other hand since a contact 72 is opened when the release button PB is pressed, the potential at the point 73 becomes high and a Schmidt trigger circuit 74 is actuated to break the current flowing through the magnet 75. Since the locking member which locks a follower screen of a shutter is dislocated as the current flowing through the magnet 75 is stopped, the follower screen runs. A synchronizing contact 28 of a stroboscope is closed in synchronism with the start of running of said follower screen, and a well known type of stroboscope control circuit 64 is actuated to light the stroboscopic tube 11b for a prescribed period of time also what is shown as 76 is a variable resistance and 77 is a capacitor.

Since a person being examined may blink even after the shutter release button PB is once pressed, an improper state display is made in such case to inform the examiner that the image of eye fundus of the eye being examined was not photographed. That is when the release button PB is pressed and the shutter control circuit 58 functions the stroboscopic tube 11b emits light. The luminous flux emitted by the stroboscopic tube 11b and reflected at a surface of the eye being examined is received by the light receiving element 3 and is applied to the amplification circuit 51. If the frequency $f_o$ of the current of the luminous flux from the light source 11a detected by the light receiving element 3 through the rotation of the chopper 66 and the frequency of the stroboscope (here it is the value obtained by dividing "1" by the light emitting time of the stroboscope) are appreciably different from each other, the signal from the amplification circuit 51 by the stroboscopic light beam will be applied only to the second comparison circuit 60. When the electric signal from the amplification circit 51 being applied into the second comparison and discrimination circuit 60 is greater than the signal corresponding to the above mentioned level $l_2$, it is entered into the circuit 62 to light the lamp 63. Also since the blinking is done rather quickly, there will be the possibility that the lighting of the lamp 63 made directly by the signal from the circuit 60 may be overlooked by the examiner, therefore the circuit 62 is provided between said second comparison circuit 60 and the lamp 63 to extend the signal from the circuit 60 for a prescribed period of time.

Figure 5:
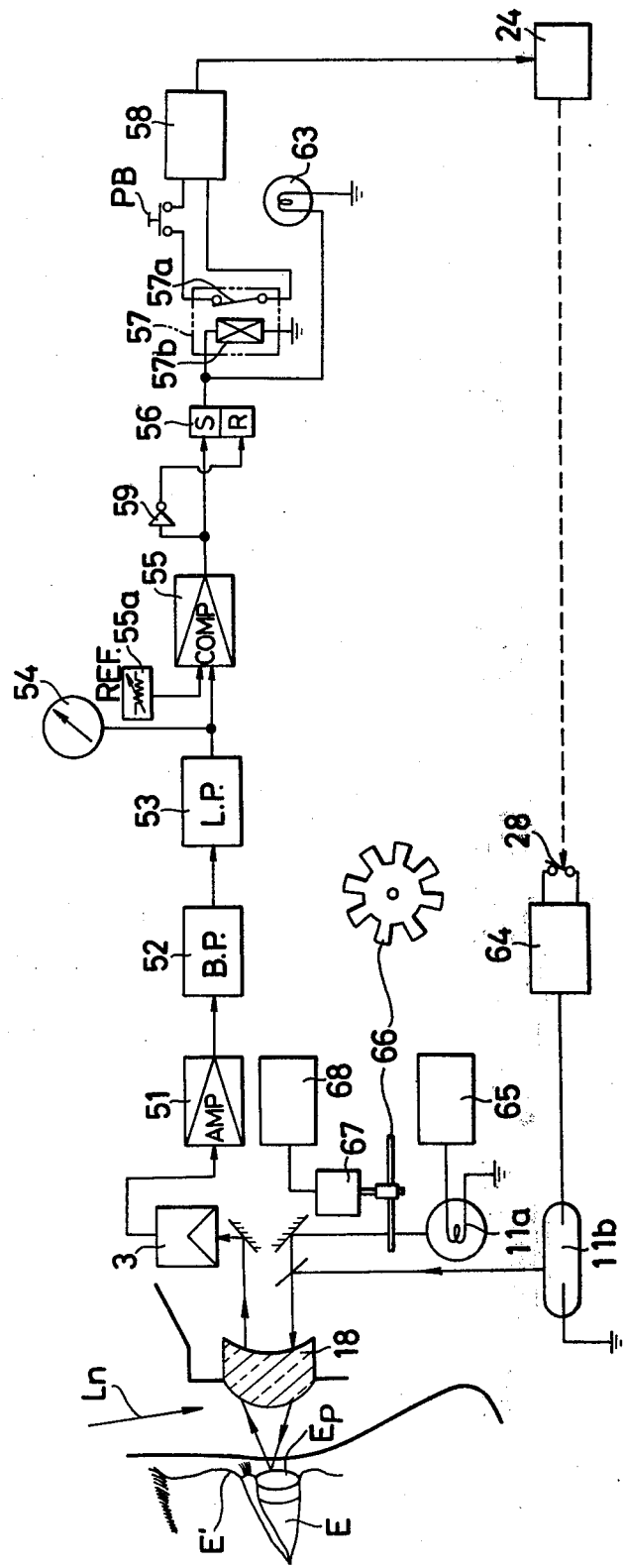
FIG. 5 is a block circuit diagram to show another example of an electric circuit to process the signal from a light receiving element in an eye fundus camera of the present invention.

When said frequency of the stroboscopic light and the frequency of the luminous flux from the illuminating light source 11a through the chopper 66 are same, the second comparison circuit 60, the comparison signal circuit 60a, the rectifier 61 and the circuit 62 are omitted, and the function of the camera will be as shown in FIG. 5. The other circuits shown in FIG. 5 are exactly same as those shown in FIG. 3. When the lighting of the lamp 63 is not necessary at a time of observation, it is possible to light the lamp 63 only for such state of the eye being examined as being closed at a time of photographing by picking up the size of signal from the smoothing circuit 53 and discriminating the same.

Figure 6:
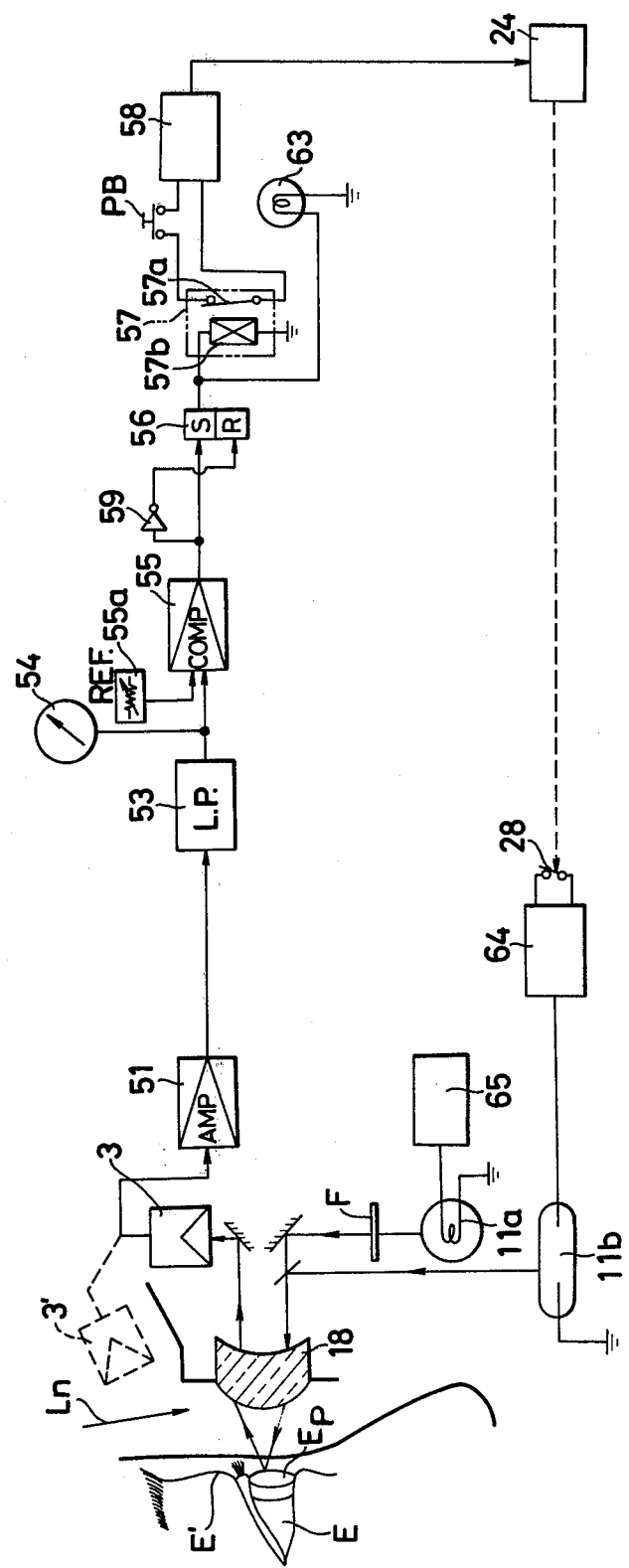
FIG. 6 is a block circuit diagram to show an example of an electric circuit to process the signal from a light receiving element when an eye fundus camera of the present invention is of aplanatic pupil type.

While the above explanations have been made on an eye fundus camera to conduct observation and photographing of an eye fundus after giving a pupil opening agent to an eye to be examined to open a pupil, even if a pupil opening agent is not given, observation for determining a spot to be photographed can be made without causing myosis by using illuminating light at the infrared zone or at rear infrared zone. And since photographing is made in a dark room in which a person being examined is placed at such case, external light Ln can be disregarded, thus the light receiving element may be placed at such position as can directly see an eye being examined at an outside of a housing of an eye fundus camera. FIG. 6 is to show chiefly an electric circuit at such case and what is shown as 3' in FIG. 1 and in FIG. 6 is a light receiving element at such time.

An infrared filter F is inserted between the tungsten bulb 11a and the condensor lens 13a to convert the observation illumination light beam into light beam at infrared zone. As an light receiving element, a photoelectromotive element having the maximum sensitivity at wavelength around near infrared zone may be advantageously used, and by doing so the light beam reflected from an eyelid can be sufficiently detected even if it is small, also even if it is not too sensitive against stroboscopic light, detection can be done satisfactorily as the amount of light emitted thereby is remarkably great.

Also since observation of image of infrared ray can not be made by a naked eye, a infrared ray image pick-up tube B is provided at a position of an eye $E_o$ being examined as shown in FIG. 1, to make observation at a picture plane of a minotor M. But when the light receiving element needs to receive great amount of reflected light, such position of the light receiving element 3 as can condense light utilizing an objective lens and a phototaking lens is advantageous.

Since the effect of external light does not exist at this time as shown in FIG. 6, a band-pass filter and a chopper to convert the outputs of the light receiving element into alternating current are not necessary. Also at this time the levels of the reflected light at a state an eyelid of a person being examined is opened and at a state the same is closed as being illuminated by infrared ray correspond respctively to A, B in FIG. 2, while those in a case of stroboscope photographing correspond to C, D in FIG. 2. The identification numbers in FIG. 6 and those in FIG. 3 are same as they represent same parts.

What is claimed is:

1. An eye fundus camera which can detect whether an eyelid of an eye being examined is opened or closed comprising:
    an illuminating optical system directing luminous flux toward the eye for illuminating the eye fundus of the eye to permit observation and photographing thereof,
    a photographing optical system directed toward the eye to photograph the eye fundus of the eye being examined,
    light receiving means in the path of light from the eye for producing an output which varies on the basis of the amount of light from the eye depending on the position of the eyelid of the eye being examined,
    detection means coupled to said light receiving means to receive the signal from said light receiving means for determining the position of said eyelid of the body being examined and producing a signal in response thereto, and
    a display means coupled to said detection means to receive signal from said detection means and to display the same.

2. An eye fundus camera according to claim 1, in which said illuminating optical system includes means to interrupt the light at predetermined intervals of time, said detection means having means to pass only the output from the receiving means which corresponds to the illuminating light being interrupted at the predetermined intervals of time.

3. An eye fundus camera according to claim 2, in which said display means has a first display means and a second display means, wherein said second display means can be seen through a finder optical system of the eye fundus camera.

4. An eye fundus camera according to claim 1, in which the luminous flux for photographing from said illuminating optical system and the luminous flux for observation have respectively wavelength zones that are different from each other.

5. An eye fundus camera which can detect whether an eyelid of an eye being examined is opened or closed comprising:
    an illuminating optical system to illuminate the eye for observation and photographing of the eye being examined,
    a photograhing optical system to photograph an eye fundus of the eye being examined,
    a light receiving means responsive to reflections from the eye and having an output which varies depending on the state of the eyelid of the eye being examined,
    a detection means coupled to the light receiving means for detecting the state of the eyelid of the eye being examined and producing a signal in response thereto,
    a shutter in the optical system,
    a shutter control circuit to control the shutter in response to the signal from said detection means, and
    display means to receive the signal from said detection means and display the same.

6. An eye fundus camera according to claim 5, in which said illuminating optical system has a means to interrupt the light at a given frequency, said detection means having means to pass only signals from said light receiving means which correspond to the given frequency.

7. An eye fundus camera according to claim 5, in which the luminous flux for photographing from said illuminating optical system and the luminous flux for observation have respectively wavelength zones that are different from each other.

8. An eye fundus camera which can detect whether an eyelid of an eye being examined is opened or closed comprising:
    an illuminating optical system to illuminate the eye for observation and photographing of an eye being examined,
    a photographing optical system to photograph an eye fundus of the eye being examined,
    a light receiving means responsive to reflections from the eye and having an output which varies depending on the state of the eyelid of the eye being examined
    a first detection means coupled to said receiving means to detect the state of the eyelid of the eye being examined by the signal from said light receiving means at a time of observation of the eye being examined,
    a second detection means coupled to said receiving means to detect the state of the eyelid of the eye being examined by the signal from said light receiving means at a time of photographing of the eye being examined, and
    a display means coupled to said second detection means to display the signal from said second detection means and to display the state of the eyelid of the person being examined at a time of photographing.

9. An eye fundus camera according to claim 8, in which said illuminating optical system has a means to interrupt the light at prescribed intervals of time, said first detection means having means to pass only the output of said light receiving means which corresponds to the illuminating light being interrupted at the predetermined intervals of time.

10. An eye fundus camera according to claim 9, in which said display means is actuated also by the signal from said first detection means.

11. An eye fundus camera which can detect whether an eyelid of an eye being examined is opened or closed comprising:
    an illuminating optical system to illuminate the eye fundus being examined for observation and photographing,
    a photographing optical system to photograph the the eye fundus of the eye being examined,
    a light receiving means to receive an amount of light varying with the state of the eyelid of the eye being examined,
    first detection means coupled to the receiving means to detect the state of the eyelid of a person being examined on the basis of the signal from said light receiving means at a time of observation of the eye being examined, second detection means coupled to the receiving means to detect the state of the eyelid of a person being examined on the basis of the signal from said light receiving means at a time of photographing the eye being examined, shutter control circuit coupled to said first detecting means to control a shutter mechanism on the basis of the signal from said first detection means, and display means coupled to said second detection means to display the signal from said second detection means.

12. An eye fundus camera according to claim 11, in which said illuminating optical system has a means to interrupt the light at prescribed intervals of time, while said first detection means has a means to pass only signals from said light receiving means which correspond to the interruption at the prescribed intervals of time.

13. An eye fundus camera according to claim 12, in which said display means is actuated also by the signal from said first detection means.

14. For an eye having a retina and a lid, a camera for observing and photographing the retina, comprising:

an illuminating optical system directed toward the eye for illuminating the retina, a photographic optical system directed toward the eye for photographing the retina, light receiving means in a path of light from the eye for producing an output which varies depending on the amount of light from the eye so as to produce a greater output when the eyelid of the eye covers the eye, detection means coupled to said light receiving means for producing a signal when the output of said light receiving means is sufficient to indicate that an eyelid covers the eye during observation of the eye, display means coupled to said detecting means to indicate when the detecting means produces the signal so as to indicate that the eye is covered by the lid.

15. An opthalmoscopic apparatus comprising an eye inspecting optical system having an objective opposing to an eye to be inspected and a lens group, an illuminating optical system for projecting a light flux to a fundus of the eye to be inspected, a fixed light receiving means having its light receiving surface positioned substantially conjugate to an eyelid of the eye to be inspected in respect to said objective and said lens group, and able to generate an electric signal corresponding to the amount of the incident light, a comparing circuit for comparing a predetermined value with said electric signal to generate a resultant signal, said predetermined value being larger than the value of the electric signal generated by said light receiving means when said light receiving surface receives light reflected by the fundus of the eye.

16. An opthalmoscopic apparatus according to claim 15, further comprising:

a shutter arranged behind said lens group, a film arranged behind said shutter, an indicating means which operates only for a period of time predetermined by said resultant signal, said illuminating optical system including an observation light source and a photographic light source 17. An opthalmoscopic apparatus according to claim 16, further comprising:

a finder system to which the light flux from said lens group is introduced during the observation of the fundus of the eye being inspected, said indicating means being arranged in a light path of said finder system.

* * * * *